United States Patent
Assaker et al.

(10) Patent No.: US 6,569,164 B1
(45) Date of Patent: May 27, 2003

(54) SPINAL OSTEOSYNTHESIS SYSTEM FOR ANTERIOR FIXATION

(75) Inventors: Richard Assaker, Kain (BE); Frédéric Conchy, Saint Médard d'Eyrans (FR); Régis Le Couedic, Cestas (FR)

(73) Assignee: Stryker Spine (FR)

( * ) Notice: Subject to any disclaimer, the term of this patent is extended or adjusted under 35 U.S.C. 154(b) by 0 days.

(21) Appl. No.: 09/674,207

(22) PCT Filed: Apr. 29, 1999

(86) PCT No.: PCT/FR99/01019

§ 371 (c)(1),
(2), (4) Date: Jan. 30, 2001

(87) PCT Pub. No.: WO99/55246

PCT Pub. Date: Nov. 4, 1999

(30) Foreign Application Priority Data

Oct. 9, 1998 (FR) .............................. 98 12662
Apr. 29, 1999 (FR) .............................. 98 05387

(51) Int. Cl.⁷ .............................................. A61B 17/56
(52) U.S. Cl. ..................... 606/61; 606/69; 606/73
(58) Field of Search ............................. 606/61, 60, 69, 606/70, 72, 73; 411/389, 537, 400, 395

(56) References Cited

U.S. PATENT DOCUMENTS

| | | |
|---|---|---|
| 4,289,123 A | 9/1981 | Dunn |
| 4,987,892 A | 1/1991 | Krag et al. |
| 5,108,395 A | 4/1992 | Laurain |
| 5,147,360 A | 9/1992 | Dubousset |
| 5,380,324 A | 1/1995 | Müller et al. |
| 5,613,968 A | 3/1997 | Lin .......................... 606/61 |
| 5,628,740 A | 5/1997 | Mullane |
| 5,662,652 A * | 9/1997 | Schafer et al. ................ 606/61 |
| 5,683,391 A | 11/1997 | Boyd |
| 5,713,898 A * | 2/1998 | Stucker et al. ................ 606/60 |
| 5,938,663 A * | 8/1999 | Petreto ........................ 606/61 |
| 6,004,322 A | 12/1999 | Bernstein |
| 6,123,706 A * | 9/2000 | Lange .......................... 606/61 |
| 6,132,431 A | 10/2000 | Nilsson et al. |
| 6,299,614 B1 * | 10/2001 | Kretschmer et al. .......... 606/60 |
| 6,328,739 B1 | 12/2001 | Liu et al. |
| 6,423,064 B1 | 7/2002 | Kluger |

FOREIGN PATENT DOCUMENTS

| | | | |
|---|---|---|---|
| DE | 195 34 136 A1 | 3/1991 | |
| DE | 94 12 744 U1 | 1/1996 | |
| DE | 4433 360 A1 | 2/1996 | |
| DE | 4433360 * | 2/1996 | .................. 606/61 |
| DE | 297 12 697 U1 | 9/1997 | |
| EP | 0 726 064 A2 | 8/1996 | |
| FR | 2 244 446 | 9/1973 | |
| FR | 2 697 744 | 5/1994 | |
| FR | 2 731 344 | 9/1996 | |
| WO | WO 94/06360 | 3/1994 | |
| WO | 96/27340 | 9/1996 | |

* cited by examiner

*Primary Examiner*—Pedro Philogene
(74) *Attorney, Agent, or Firm*—Lerner, David, Littenberg, Krumholz & Mentlik, LLP

(57) ABSTRACT

The invention concerns a backbone osteosynthesis system comprising an elongated element, a vertebral screw, and a connecting element comprising two branches for clamping between them the linking element, at least one first branch being capable of being engaged onto the screw. The system comprises a second vertebral screw, the first branch having an extension capable of being engaged onto the second screw. The system may comprise a second elongated linking element.

32 Claims, 8 Drawing Sheets

FIG_2

FIG_7

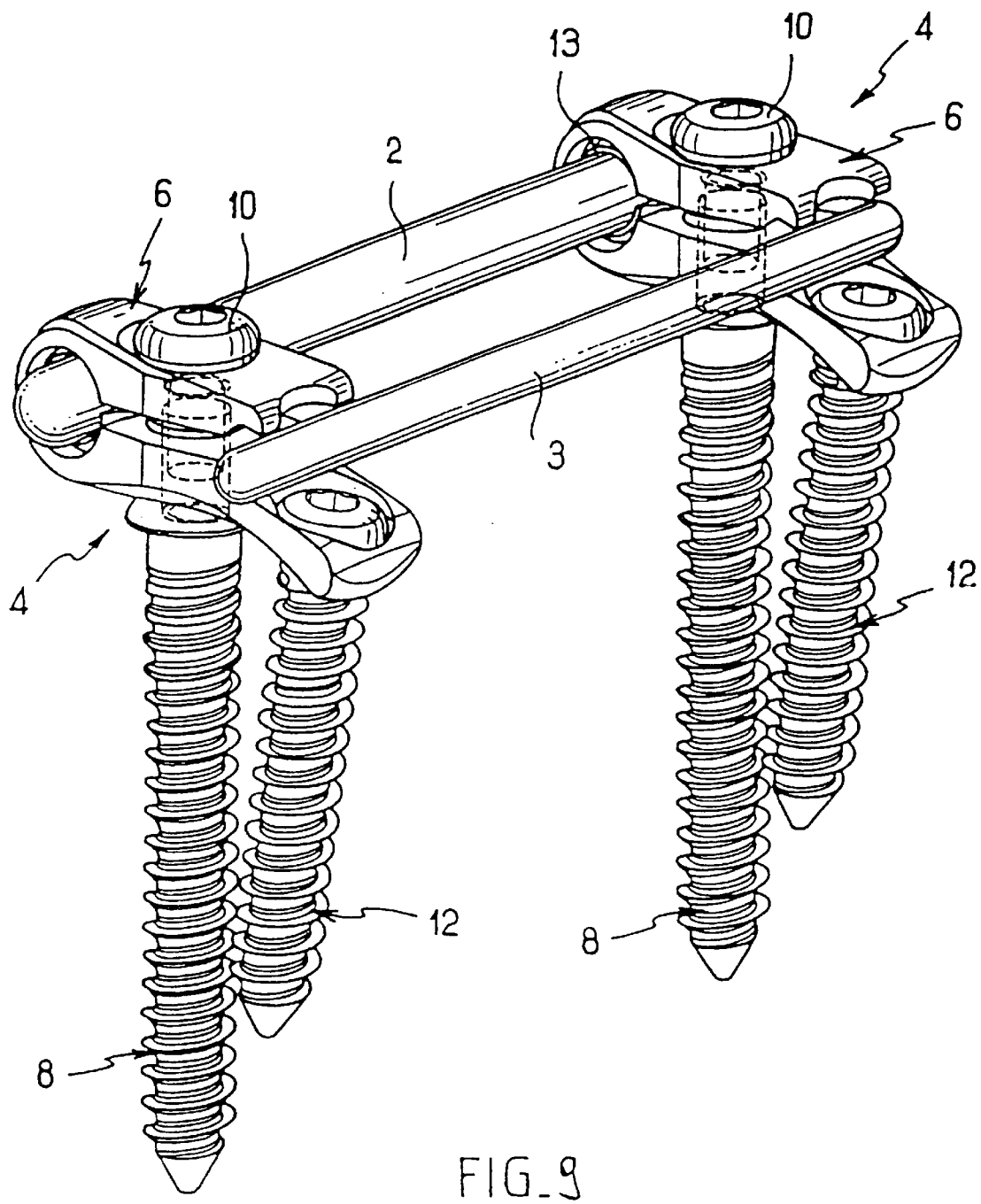
FIG_9

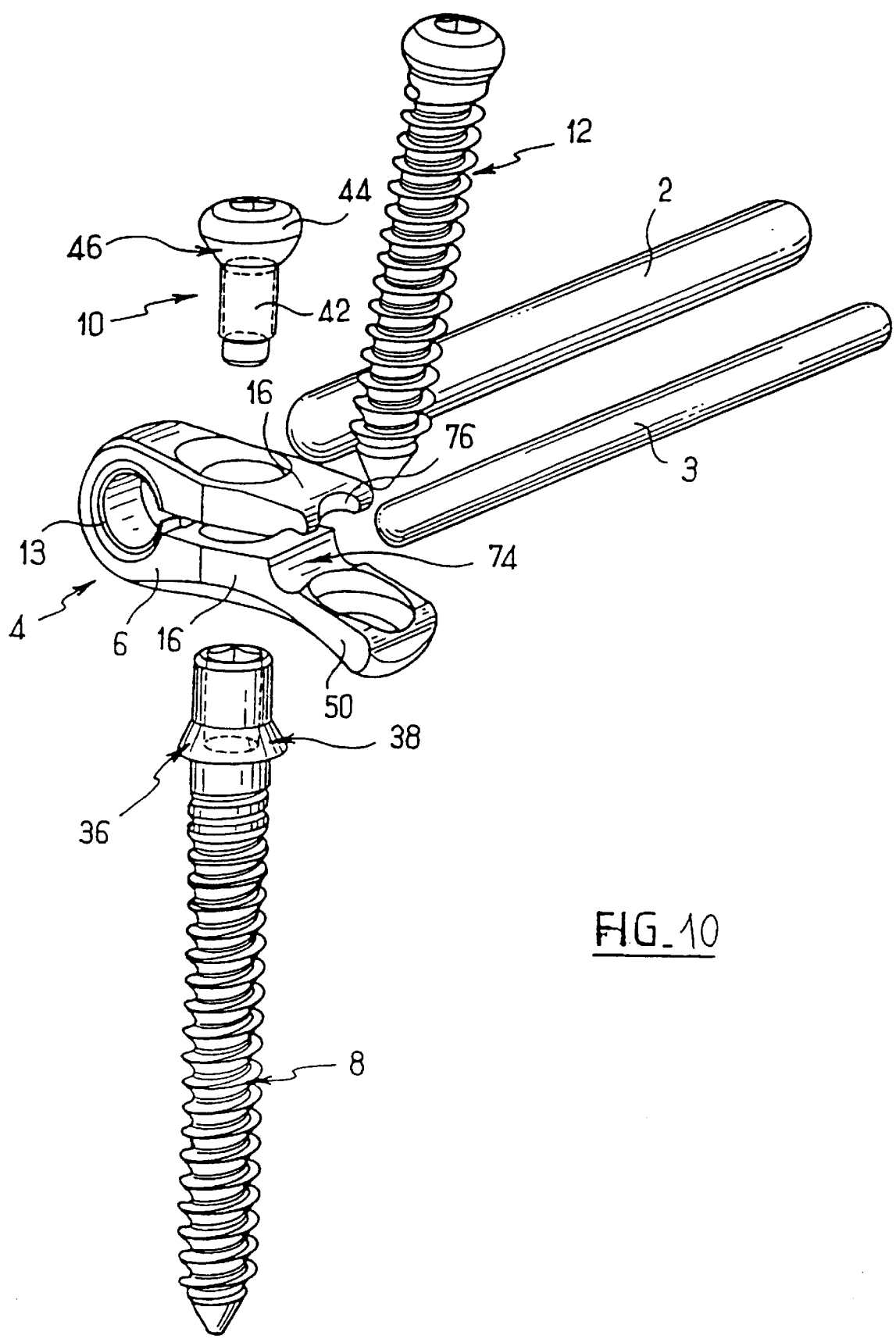
FIG_10

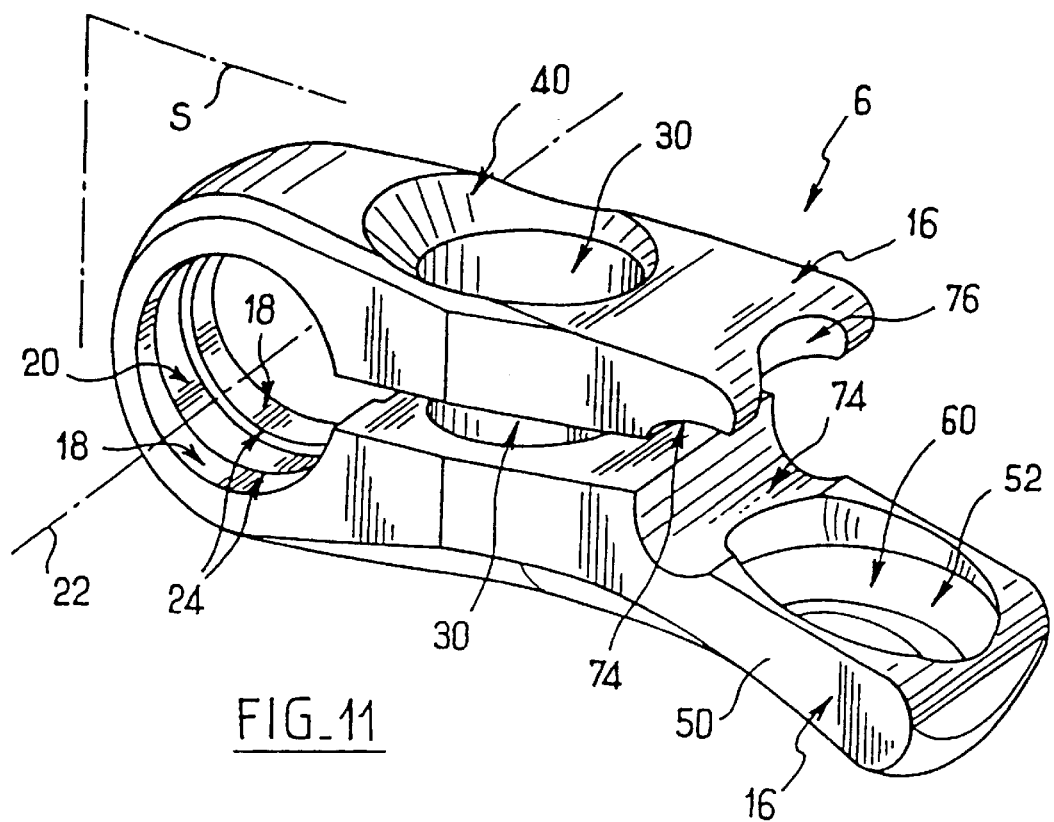
FIG_11
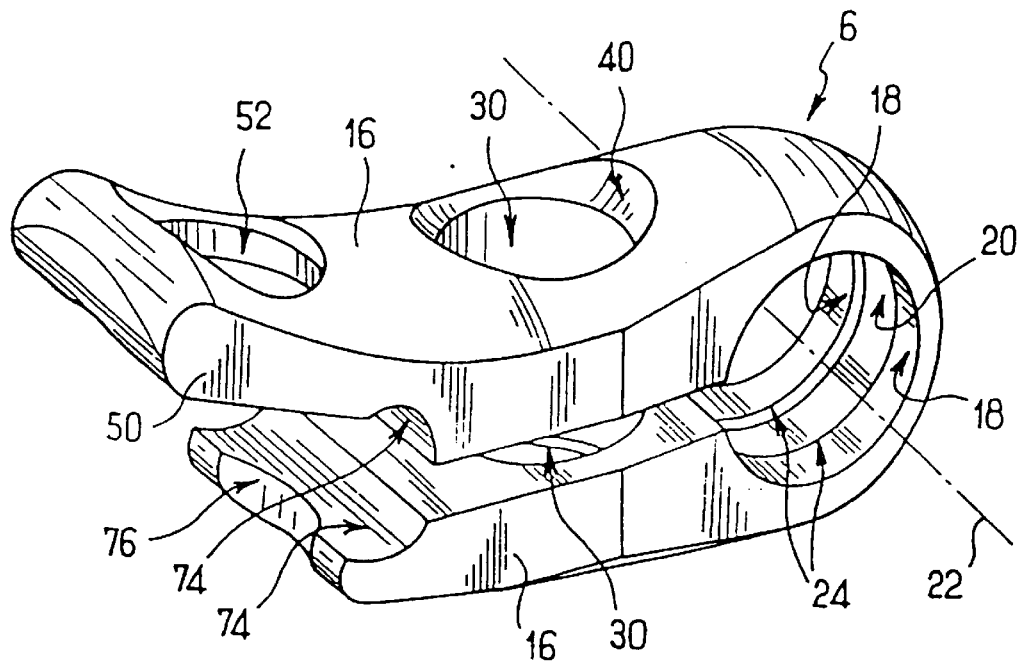
FIG_12

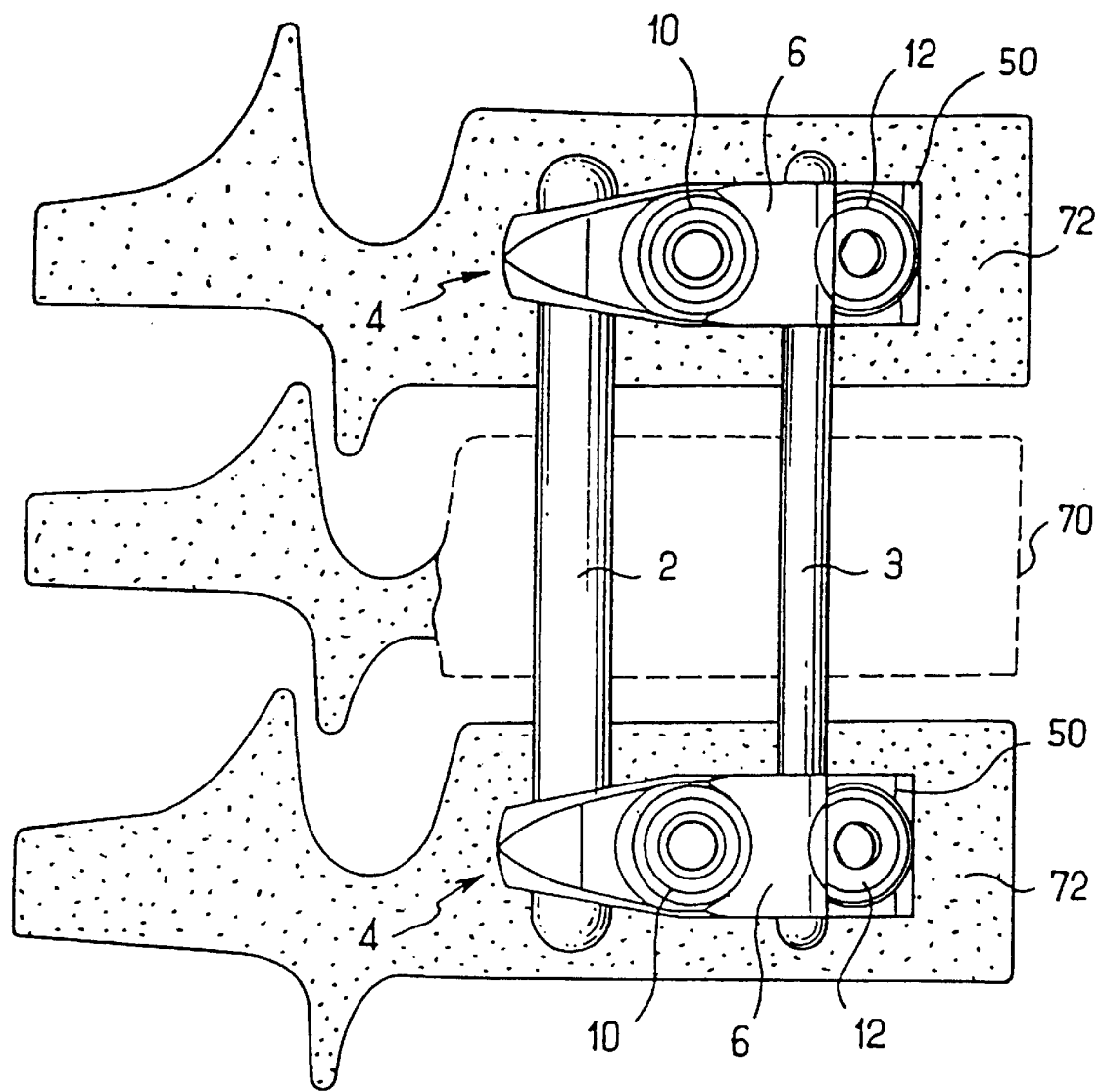
FIG_13

SPINAL OSTEOSYNTHESIS SYSTEM FOR ANTERIOR FIXATION

The invention concerns spinal osteosynthesis systems, in particular for anterior fixation.

Spinal osteosynthesis systems for anterior fixation are known in which the connection elements are formed by plates, and others are known in which the connection elements are formed by rods. Because of their bulk, the systems based on plates are difficult to use, if they can be used at all, via the endoscopic route. Moreover, their limited size (length) means that they can only be used for simple vertebrectomies involving a single vertebra, or perhaps two. It is impossible to treat scoliosis with this type of implant. Finally, the plates are difficult to adapt to the morphology of the vertebra in which they are anchored. Moreover, the systems based on rods generally comprise fairly voluminous connectors which cannot always be used via the endoscopic route.

A spinal osteosynthesis device is also known from document FR-2,731,344, the counterpart of WO-96/27340, which device comprises a connector with two branches which can clamp a connection rod between them, the branches being able to be engaged on a vertebral pedicle screw. However, this connector, while well suited for posterior fixation of the spine on the vertebral pedicles, does not ensure sufficient stability with a view to anterior fixation of the spine.

An object of the invention is to make available a spinal osteosynthesis system of a different type, adapted for anterior fixation, easy to fit, ensuring good stability of the system on the spine, and compatible with being fitted via the endoscopic route.

To achieve this object, the invention provides a spinal osteosynthesis system comprising an elongate connection element, a vertebral screw, and a connector including two branches which are able to clamp the connection element between them, at least a first of the branches being able to be engaged on the screw, the system comprising a second vertebral screw, the first branch having an extension which can be engaged on the second screw.

Thus, the connector can be rendered less voluminous so that it can be put into place via the normal or endoscopic route. Moreover, the fixation of the connector to the vertebra by means of the two screws permits precise, stable and reliable positioning of the connector and thus of the connection element. This connector is easy to join to the connection element and to the screws. These advantages make this connector particularly well suited to anterior fixation of the spine. The connector will preferably be in one piece.

Advantageously, the extension has an opening for receiving the second screw.

Advantageously, the extension has a spherical recess at one edge of the opening intended to be remote from the vertebra.

Thus, it is possible to control the angle of the second screw relative to the connector in order to better adapt the system to the configuration of the vertebra.

Advantageously, one of the branches which is intended to be remote from the vertebra has an opening for receiving the first screw, and a spherical recess at one edge of the opening intended to be remote from the vertebra.

Thus, it is possible to control the angle of the first screw relative to the connector in order to better adapt the system to the configuration of the vertebra.

Advantageously, the extended branch can be bent manually, in particular using a tool.

Thus, it is possible to adapt the shape of the connector to that of the vertebra and in particular to position the connector very close to the latter.

Advantageously, the first screw includes a head and a flange distinct from the head and able to cooperate with one of the branches which is intended to be adjacent to the vertebra, in order to immobilize the connector in terms of rotation relative to the first screw.

Thus, upon fitting, prior immobilization of the connector relative to the first screw is obtained, facilitating the positioning of the other elements and making it possible to effect positional corrections, all this before final clamping of the fitted system.

Advantageously, the flange has a face, which is in particular a conical face, able to immobilize the connector by friction.

Advantageously, the first screw has a threaded orifice, the system comprising a clamping screw which can constitute a screw-nut connection with this orifice and is able to bear on one of the branches which is intended to be remote from the vertebra in order to clamp the branches.

Thus, it is possible first to fit the first screw, the connector and the second screw, and only later to install the clamping screw in order to proceed with clamping of the assembly.

Advantageously, the system comprises a ring which can be engaged on the rod and received between the branches, the connector and the ring being designed to permit control of the orientation of the rod in two mutually perpendicular planes before the branches are clamped.

Advantageously, the two branches form part of a single component which is elastically deformable in order for the branches to be closed towards each other.

Advantageously, the connector can be fixed to the vertebral screw and to the first connection element by choosing an angular position of the connection element relative to the connector.

It has also been noted that the device in document FR-2,731,344 mentioned above does not always afford sufficient rigidity for anterior fixation of the spine.

Consequently, a subsidiary object of the invention is to provide a system suited for anterior fixation and ensuring a particularly high degree of rigidity.

To achieve this object, the system advantageously comprises a second elongate connection element, the connector being able to be fixed simultaneously to the two connection elements.

Thus, the presence of the two connection elements gives the system very great rigidity, without complicating its assembly, without increasing the volume of its various components (which renders it compatible with fitting via the endoscopic route), and while maintaining the possibility of controlling the angular position of the connector relative to the first connection element. The system according to the invention does not require identical bending on the two connection elements. Moreover, the number of connectors can remain small.

Advantageously, the system is designed in such a way that the second connection element can be fixed to the connector only in a single angular position relative to the connector.

Thus, the shape of the second connection element dictates the relative angular position of the connectors which are fixed to it. This angular position can therefore be chosen in advance depending on the prior curvature given to this connection element, either at the time of manufacture or, better still, during the surgical intervention.

Advantageously, the second connection element has less resistance to bending than the first connection element.

Thus, the first connection element has mainly a function ensuring support of the connectors, and the second connection element has mainly a function ensuring relative angular positioning of the connectors.

Advantageously, the branches can simultaneously clamp the two connection elements.

Advantageously, the system is designed in such a way that the second connection element, when fixed to the connector, extends in a trajectory of the second vertebral screw for its disengagement from the connector.

Thus, the second screw is prevented from starting to come out at an inopportune moment.

Advantageously, the system comprises a second connector, the two connectors each being able to be fixed simultaneously to the two connection elements.

Advantageously, the system is intended to be fixed on the anterior part of the spine.

The invention also provides a connector for a spinal osteosynthesis system, including two branches which can clamp an elongate connection element between them, at least a first of the branches having an opening which can be engaged on a vertebral screw, and in which the first branch has an extension having an opening which can be engaged on a second vertebral screw.

This connector is adapted to form part of the system according to the invention.

Other characteristics and advantages of the invention will become more apparent from the following description of two preferred embodiments given as nonlimiting examples. In the attached drawings:

FIG. 5 is a view, half in elevation and half in axial section, of a ring of the system in FIG. 1;

FIG. 6 is a view, partly from above and partly in section, of the connector in FIG. 3 receiving the rod;

FIG. 7 is a partial perspective view showing the head of the main screw;

FIG. 9 is a perspective view of the system according to a second embodiment of the invention;

FIG. 10 is a partial and exploded perspective view of the system in FIG. 9;

FIGS. 11 and 12 are two perspective views, from above and below, respectively, showing one of the connectors of the system in FIG. 9; and FIG. 13 shows the system from FIG. 9 fixed on vertebrae.

Figure 1:
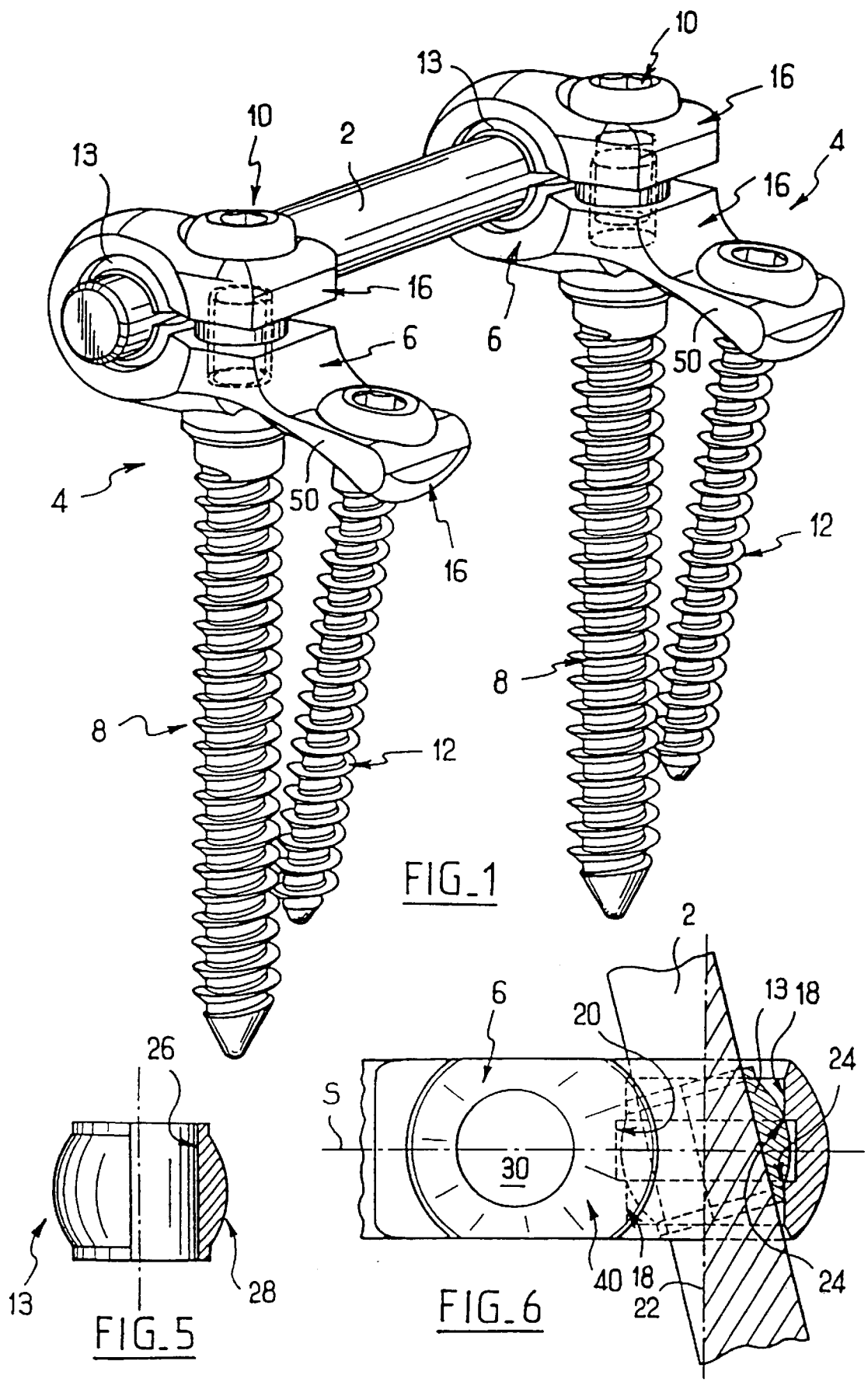
FIG. 1 is a perspective view of the system according to a first embodiment of the invention.
Figure 2:
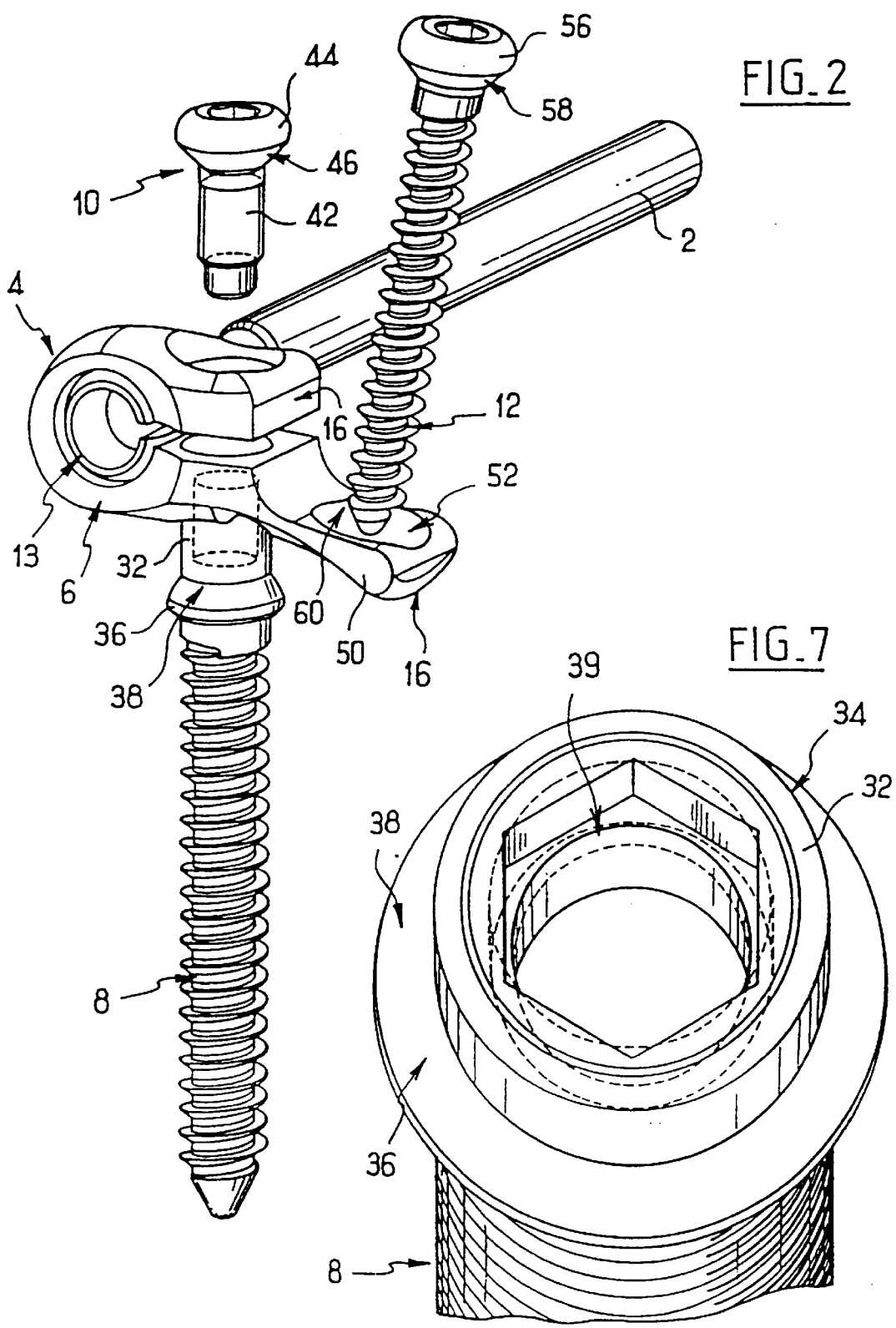
FIG. 2 is a partial and exploded perspective view of the system in FIG. 1.

Referring to FIGS. 1 to 8, the system according to the invention comprises, in the first embodiment, an elongate connection rod 2 of circular cross section and several connector sub-assemblies 4 which can be fixed to the latter. Each of these sub-assemblies, of which two can be seen in FIG. 1 and of which one can be seen in FIG. 2, comprises a connector 6, a first vertebral screw or main screw 8, a clamping screw 10, a second vertebral screw or secondary screw 12, and a ring 13.

Figure 3:
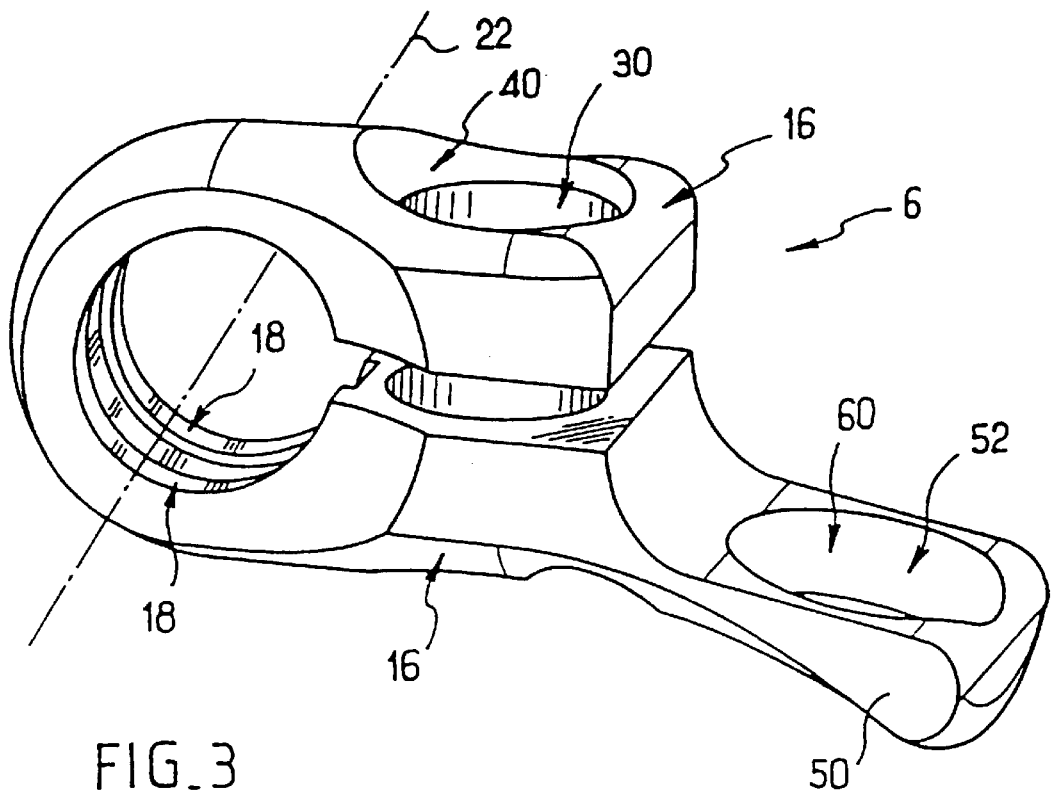
FIGS. 3 and 4 are two perspective views, from above and below, respectively, showing one of the connectors of the system in FIG. 1.
Figure 4:
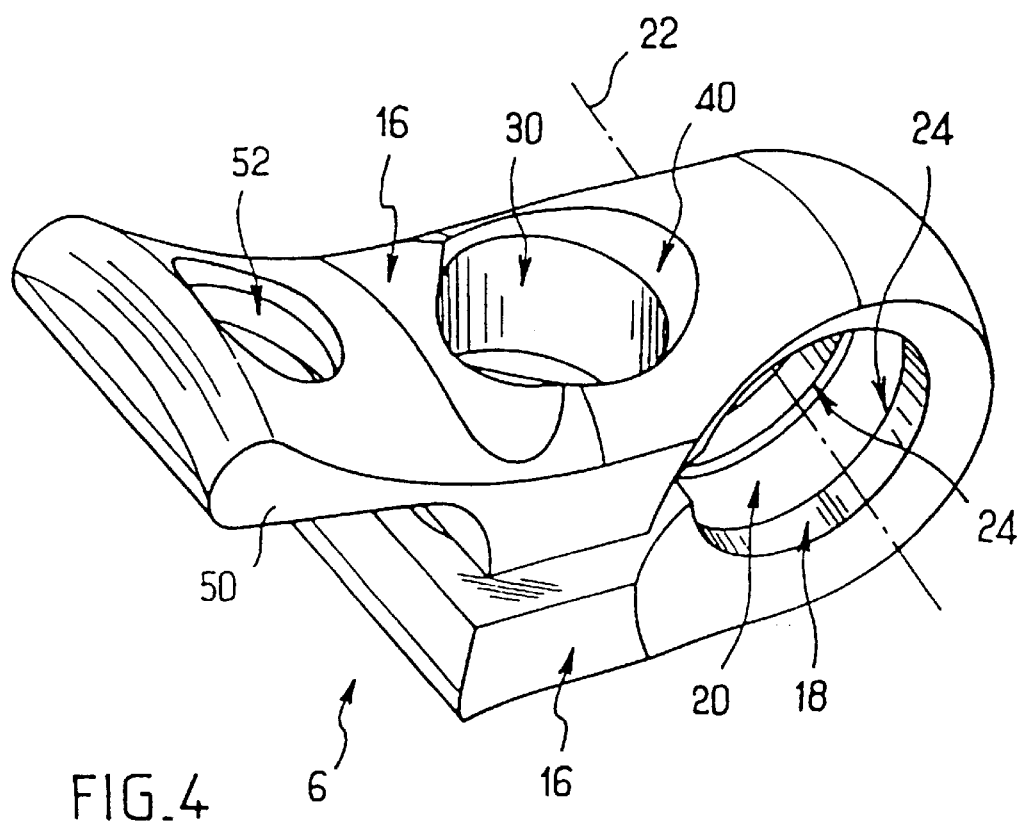

Referring to FIGS. 3 and 4, the connector 6 includes two branches 16 extending opposite to and at a distance from each other, giving the connector a general U-shaped profile. The connector 6 includes a plane of symmetry S perpendicular to the width of the branches 16 and parallel to their length. Referring to FIG. 6, at the point of origin of the branches 16 the connector has two cylindrical and coaxial inner faces 18, 20 with axis 22 perpendicular to the plane S and with different radii, the face 20 of greater radius being in two distinct parts and extending on either side of the face 18 of lesser radius, which is traversed by the plane S. At their junctions, the two faces 18, 20 form two circular edges 24 with axis 22.

The ring 13 has a cylindrical inner face 26 and a spherical outer face 28 which are coaxial. The cylindrical inner face 26 has a radius about equal to that of the rod 2 in such a way that the ring 13, slotted on one side along its axis, can be received as a sliding fit on the rod. Moreover, the ring 13 can be lodged between the branches 16 opposite the cylindrical faces 18, 20. The spherical outer face 28 of the ring has a radius which is adapted such that in this position the edges 24 of the connector 6 are in linear contact with the spherical outer face 28 of the ring 13 and serve as bearings for it. In this position, before clamping of the branches 16, the angular position of the rod 2 engaged in the ring 13 can be controlled in two mutually perpendicular planes over an amplitude of, for example, 15° on either side of a mean position of the rod in which the rod is perpendicular to the plane S.

The branches 16 have two respective smooth cylindrical openings which, in this case, are through-orifices 30 extending coaxially opposite each other. The main screw 8 is a bicortical vertebral screw and has a threaded body for this purpose, in a manner known per se. It has a head 32 having a smooth cylindrical outer face 34. At the junction between the head and the body, the screw includes an annular flange 36 having a plane lower face perpendicular to a longitudinal axis of the screw and a frustoconical upper face 38 with the narrowest cross section of the frustum situated towards the head 32 of the screw. The head 32 has a threaded orifice 39 coaxial to the body of the screw and, formed in the threaded face of the orifice 39, a noncircular shape such as a hexagon socket. The clamping screw 10 includes a threaded body 42 which is able to form a screw-nut connection with this orifice 39, and a screw head 44 in which a hexagon socket is formed. The head 44 has a spherical and convex lower outer face 46 whose narrowest cross section is situated towards the point of the screw.

One of the branches 16, which for the sake of clarity we will here call the lower branch, has an extension 50 extending in the direction away from the cylindrical faces 18, 20 of the connector. This is the branch intended to be adjacent to the vertebra. The two branches 16 are able to be engaged simultaneously on the head 32 of the main screw 8 introduced starting from the lower branch against which the upper face 38 of the flange 36 comes into abutment. The clamping screw 10 is then introduced into the head 32 of the main screw 8 starting from the upper branch 16. The tightening of the screw 10 in the head 32 of the main screw 8 causes the branches 16 to close towards each other and causes frictional blocking of the rod 2 in the chosen position relative to the connector 6.

The orifice 30 of the lower branch 16 has a lower edge, remote from the upper branch and intended to be towards the vertebra, having a concave spherical recess 40 intended to come into contact with the upper face 38 of the flange 36 in order to effect, by friction, rotational blocking of the connector 6 relative to the axis of the main screw 8. The orifice 30 of the upper branch 16 has an upper edge, remote from the lower branch and intended to be remote from the vertebra, having a concave spherical recess 40 intended to come into contact with the convex and spherical lower face 46 of the head 44 of the clamping screw 10 and making it possible to fix the latter and the main screw 8 by controlling the angular orientation of the main screw 8 relative to the connector.

The extension 50 has an opening in the form of a through-orifice 52. The lower branch 16 is curved in the area of the extension 50 in a direction away from the upper branch 16 in such a way that the axes of its orifices 30 and 52 are not quite parallel. The secondary screw 12 is a vertebral screw, here a monocortical screw, having a threaded body and a head 56 with a spherical and convex lower face 58 whose narrowest cross section is situated towards the body. Its head has a hexagon socket. The orifice 52 of the extension has an upper edge, oriented towards the other branch 16 and intended to be remote from the vertebra, having a spherical and concave recess 60 intended to come into contact with the spherical and convex lower face 58 of the head 56 of the secondary screw 12, making it possible to control the angular orientation of this screw relative to the connector 6.

Certain characteristics of the connector 6 which have not been expanded on in detail here will be found in the abovementioned related documents FR-2,731,344 and WO-96/2730.

The lower branch 16 can be bent in order to accentuate or reduce its curvature for better adaptation to the shape of the anterior part of the vertebra for which it is intended. Once bent, this branch 16 is no longer stressed in flexion since it is fixed to the vertebra by two screws 8, 12 along its length. The two screws, namely the main screw 8 and the secondary screw 12, are self-tapping and include bone threads.

In an alternative embodiment, the main screw 8 does not have a hexagon socket in its threaded orifice 39, and instead the flange 36 has a hexagonal shape or has two parallel and diametrically opposite flats which can cooperate with a tightening wrench for rotating this screw 8 relative to the connector 6.

In the present example, the connector 6 is made in one piece. The different parts of the system are made of biocompatible metal.

Figure 8:
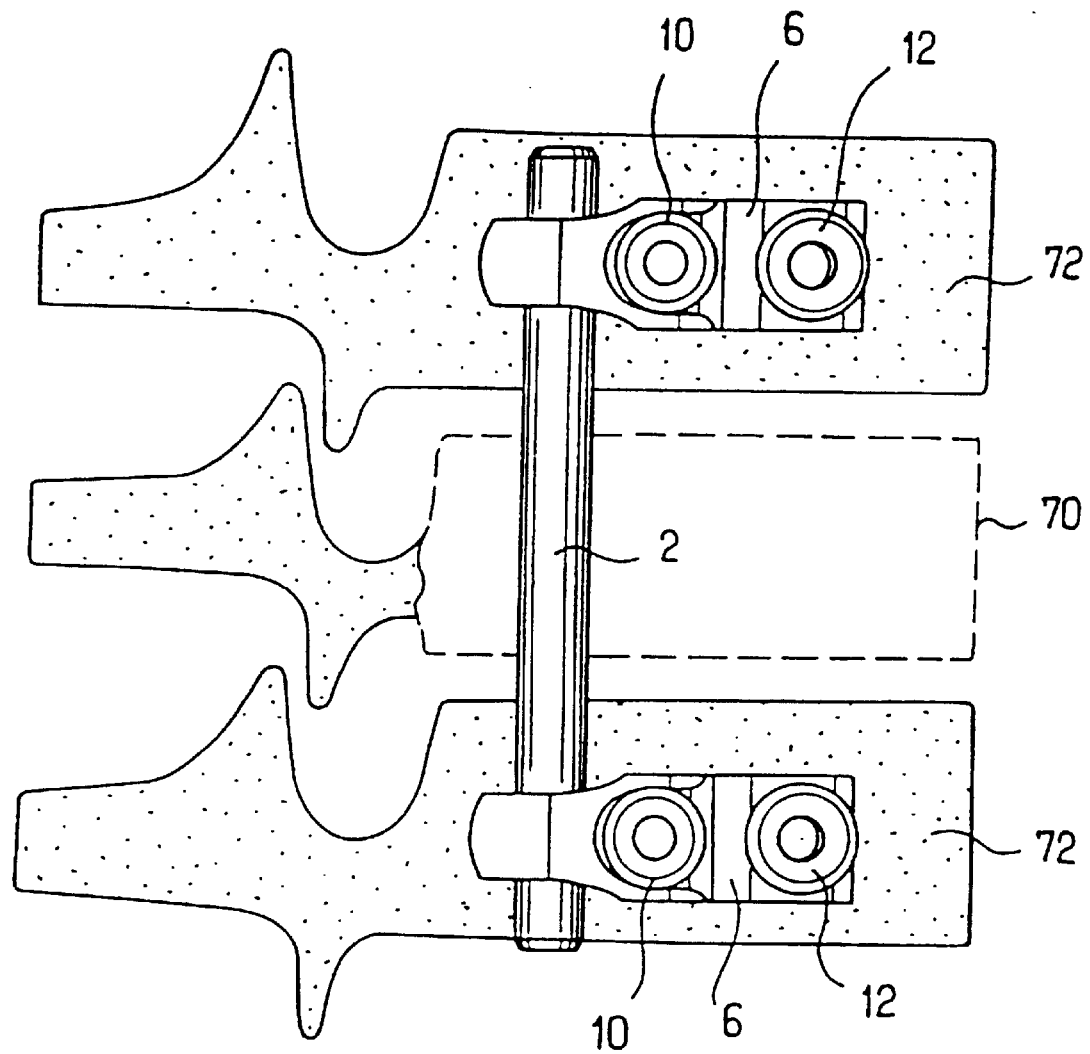
FIG. 8 shows the system from FIG. 1 fixed on vertebrae.

Such a device is fitted in the following manner, with reference to FIG. 8. After exposing the affected vertebra 70 and the two adjacent vertebrae 72, a vertebrectomy is performed while preserving, if possible, the respective plates of these vertebrae. For each subassembly, a pilot hole is made on the lateral side of the associated vertebra 72 at an equal distance from the upper and lower plates, and at the limit of the most posterior quarter of the vertebral body. The main screw 8 is then inserted into this pilot hole as far as the limit flange 36. The connector 6 is then positioned on the said main screw 8, blocked in translation by the conical face 38 of the said main screw 8 matching the recess 40 of the connector 6. The fit of the connector 6 on the vertebra is then checked and can be adjusted by withdrawing the said connector in order to bend the lower branch 16 which is its most anterior part.

The secondary screw 12 is then screwed relative to the main screw 8 into the second orifice 52 of the lower branch 16 until the spherical seat 60 of the extension, provided for this purpose, comes into contact with the spherical part 58 of the said secondary screw 12. It is desirable to position the connector 6 as parallel as possible to the plates.

After the two adjacent vertebrae 72 have been thus equipped, the rod 2 is positioned in the rings of the connectors 6 and its angular position on each sub-assembly is controlled. Final clamping is effected by virtue of the clamping screw 10 which is inserted into the main screw 8 and thereby compresses the connector 6 in order to clamp the rod.

In the second embodiment illustrated in FIGS. 9 to 13, the system is very similar to that of the first embodiment. However, it is distinguished by the presence of a second elongate connection rod 3 or secondary rod of circular cross section, and by the adaptation of the connector 6 for receiving this second rod. The ring 13 is received on the first rod or main rod 2.

The two connection rods 2, 3 each have a profiled rectilinear shape, the profile here being circular. The secondary rod 3 has a cross section, transverse to its longitudinal axis, having a diameter smaller than that of the main rod 2. The main rod 2 will, for example, have a diameter of 6 mm. The diameter of the secondary rod 3 will, for example, be between 30% and 80% of the diameter of the main rod 2. This small diameter allows the surgeon to choose the curvature of the secondary rod 3 corresponding to that of the level of the spine which is being operated on. By contrast, since the rings 13 allow relative angular positioning of the two connectors 6, the main rod 2 does not have to be bent. It can thus have a substantial diameter in order to be very robust.

The branches 16 of the connector have respective cylindrical recesses or jaws 74 formed in the faces of the branches opposite each other. The recesses 74 extend opposite each other and have axes parallel to each other and perpendicular to the plane of symmetry S.

On the upper branch 16, the recess 74 extends at a free end of the branch such that the orifice 30 is interposed between the faces 18, 20, on the one hand, and the recess 74 on the other. On the lower branch 16, the recess 74 extends between the two orifices 30 and 52, at the origin of the extension 50. It is contiguous with the orifice 52 so that it engages on its edge 60.

The secondary rod 3 is intended to be received in the recess 74 of the lower branch 16 in a unique angular position relative to the connector, perpendicular to the plane of symmetry S. When the two branches 16 are clamped in the direction of each other, the recess 74 of the upper branch comes into contact with the secondary rod 3 which is thus in surface contact with each of the two recesses, which effect frictional blocking of the secondary rod 3 relative to the connector 6, which are thereby rigidly fixed to each other.

The secondary rod 3 is placed in the recess 74 of the lower branch after the secondary screw 12 has been introduced into the orifice 52. The position of the recess 74 of the lower branch is such that the secondary rod 3 then extends in the trajectory of the head of the secondary screw 12 for its disengagement from the connector and its exit from the orifice 52. Consequently, once the secondary rod 3 has been fixed to the connector, the secondary screw 12 can no longer be separated from the connector.

The upper branch 16 of the connector has at its free end a notch 76 which engages on the recess 74 with which it is contiguous and facilitates manoeuvring of the secondary screw 12 by means of a tool despite the space occupied by the upper branch.

The system according to the second embodiment is fitted in a similar way to the system of the first embodiment. The placement of the main screw 8 and of the secondary screw 12 remains unchanged.

After the two adjacent vertebrae 72 have been equipped, the main rod 2 is positioned in the rings 13 of the connectors 6 and the angular position of each sub-assembly 4 relative to this rod 2 is controlled. The secondary rod 3 is then introduced into the recesses 74 of the connectors 6 after it has first been bent manually to obtain the curvature required for the corresponding level of the spine. In the event of an error, this rod 3 can be removed in order to correct its curvature and then put back in place. FIG. 9 shows the system before the clamping of the branches. Final clamping is effected by virtue of the clamping screw 10 which is inserted into the main screw 8 and thereby compresses the connector 6 in order to clamp its two branches 16 towards each other. During this clamping, the clamping force is directed first on the main rod 2 via the ring 13, until the recess 74 of the upper branch comes into contact with the secondary rod 3. Thereafter, the clamping force is distributed on the two rods 2, 3. Thus, the reaction at the level of the pairing of main screw 8 and clamping screw 10 is substantially coaxial to these.

When the system is in place, the connectors 6, of which there are at least two, are each rigidly and simultaneously fixed to the same main rod and secondary rod.

The characteristics relating to the association of the first screw 8 with the clamping screw 10 will be able to be implemented independently of the presence of the extension 50 and of the second screw 12.

Although less advantageous, the extended branch can be the one which is intended to be farthest from the vertebra.

The characteristics relating to the presence of the two vertebral screws on the connector will be able to be implemented independently of those relating to the presence of the main and secondary rods, and vice versa.

What is claimed is:

1. A spinal osteosynthesis system, in particular for anterior fixation, comprising an elongate connection element, a first vertebral screw, and a connector including two branches which are able to clamp the connection element between them adjacent a first end of each branch, at least a first of the branches being able to be engaged on the screw, a second vertebral screw, the first branch having an extension with an opening therein which can be engaged on the second screw the first and second screw being spaced towards a second end of said first branch from said connection element at said first end of said branch.

2. The system according to claim 1 wherein the extension has a spherical recess formed around the opening on a surface of said first branch intended to face away from the vertebra.

3. The system according to claim 2 wherein the extension has a spherical recess at one edge of the opening intended to be remote from the vertebra.

4. The system according to any one of claims 1 to 3 wherein one of the branches which is intended to be remote from the vertebra has an opening for receiving the first screw and a spherical recess at one edge of the opening intended to be remote from the vertebra.

5. The system according to claim 1 wherein the extended branch can be bent manually, in particular using a manually operated tool.

6. The system according to claim 1 wherein the first screw includes a head and a flange distinct from the head and able to cooperate with one of the branches which is intended to be adjacent to the vertebra, in order to immobilize the connector in terms of rotation relative to the first screw.

7. The system according to claim 6 wherein the flange has a face which is a conical face, able to immobilize the connector by friction.

8. The system according to claim 1 wherein the first screw has a threaded orifice, the system further comprising a clamping screw which can constitute a screw-nut connection with this orifice and is able to bear on one of the branches which is intended to be remote from the vertebra in order to clamp the branches.

9. The system according to claim 1 further comprising a ring which can be engaged on the rod and received between the branches, the connector and the ring being designed to permit control of the orientation of the rod in two mutually perpendicular planes before the branches are clamped.

10. The system according to claim 1 wherein the two branches form part of a single component which is elastically deformable in order for the branches to be closed towards each other.

11. The system according to claim 1 wherein the connector can be fixed to the vertebral screw and to the first connection element by choosing an angular position of the connection element relative to the connector.

12. The system according to claim 1 further comprising a second elongate connection element, the connector being able to be fixed simultaneously to the two connection elements.

13. The system according to claim 12 wherein the second connection element can be fixed to the connector only in a single angular position relative to the connector.

14. The system according to claim 12 or 13 wherein the second connection element has less resistance to bending than the first connection element.

15. The system according to claim 12 or 13 wherein the branches can simultaneously clamp the two connection elements.

16. The system according to claim 12 or 13 wherein the second connection element, when fixed to the connector, extends in a trajectory of the second vertebral screw for its disengagement from the connector.

17. The system according to claim 12 or 13 further comprising a second connector, the two connectors each being able to be fixed simultaneously to the two connection elements.

18. A connector for a spinal osteosynthesis system comprising first and second branches which can clamp an elongate connection element between them adjacent a first end of first branch, at least the first branch having a first opening which can be engaged on a vertebral screw, the first branch has an extension having a second opening which can be engaged on a second vertebral screw the first and second opening on said first branch are spaced from said elongate connection element towards a second end of said first branch.

19. A spinal system comprising:
   an elongate connecting rod;
   a first vertebral screw for insertion into a vertebra;
   a connector for connecting said rod and said first screw, said connector having a first branch for location adjacent the vertebra and a second branch, said branches having facing surfaces adjacent a first end of said first branch for engaging said rod;
   a clamping element acting on said first and second branches to clamp said rod therebetween; and
   a second vertebral screw, said first and second vertebral screws engaging said first branch at points thereon spaced from said rod towards a second end of said first branch.

20. The spinal system as set forth in claim 19 wherein said first and second branches are integrally connected by a U-shaped section, said U-shaped section engaging said rod.

21. The spinal system as set forth in claim 20 wherein said first vertebral screw has a head portion for engaging a vertebra facing surface surrounding an opening on said first branch.

22. The spinal system as set forth in claim 21 wherein said vertebra facing surface has a recess for engaging the head of said first screw.

23. The spinal system as set forth in claim 22 wherein said head of said first screw lockingly engages said recess to prevent the further movement of said screw with respect to said connector.

24. The spinal system as set forth in claim 21 wherein the head portion of said first screw has an internal thread.

25. The spinal system as set forth in claim 24 wherein said system, further includes a threaded clamping element for engaging said second branch and for insertion through an orifice therein into the threaded head of said first screw so that the first and second branches may be moved together by the threaded engagement of said clamping element and said first screw.

26. The spinal system as set forth in claim 19 wherein said first branch has a concave vertebra facing surface.

27. The spinal system as set forth in claim 26 wherein said first and second vertebral screws are inserted through first and second orifices in said first branch spaced along said concave surface from one another.

28. The spinal system as set forth in claim 27 wherein a longitudinal axis of said first and second screws after insertion through said orifices are not parallel.

29. A method for connecting a spinal rod to a vertebra comprising:

inserting a first vertebral screw into the vertebra, said screw having a head;

positioning a vertebral facing surface surrounding a first orifice in a first branch of a connector having first and second branches on the head of said first screw, said branches encompassing a rod receiving portion;

inserting a second vertebral screw into the vertebra through a second orifice in said first branch of said connector;

inserting a rod into said rod receiving portion;

inserting a clamping element through an orifice in said second branch and into clamping engagement with the head of said first vertebral screw; and clamping said first and second branches together with said rod therebetween by the engagement of said clamping element and said first screw head.

30. The method as set forth in claim 29 wherein said rod has a portion extending over a second vertebra wherein the method further includes connecting said rod to said second vertebra with a second connector and a vertebral screw associated therewith.

31. The method as set forth in claim 29 wherein said clamping element is a screw and said head of said first vertebral screw has a threaded recess for engagement with said clamping screw.

32. The method as set forth in claim 29 wherein said rod is located at a first end of said first branch and said first and second orifices of said first branch are located between said rod and a second end of said first branch.

* * * * *

UNITED STATES PATENT AND TRADEMARK OFFICE
CERTIFICATE OF CORRECTION

PATENT NO.    : 6,569,164 B1
DATED         : May 27, 2003
INVENTOR(S)   : Richard Assaker, Frédéric Conchy and Régis Lecouëdic It is certified that error appears in the above-identified patent and that said Letters Patent is hereby corrected as shown below:

Column 1,
Line 3, insert -- CROSS-REFERENCE TO RELATED APPLICATIONS --
Line 4, insert -- This application is the National Stage of International Application No. PCT/FR99/01019, filed April 29, 1999, the disclosure of which is hereby incorporated by reference herein. --
Line 5, insert -- BACKGROUND OF THE INVENTION --
Line 21, after "FR-2 731, 344" insert -- and its U.S. equivalent 5,938,663 --.
Line 21, "counterpart" should read -- counterparts --.

Column 3,
Line 27, insert -- BRIEF DESCRIPTION OF THE DRAWINGS --.
Line 53, insert -- DESCRIPTION OF THE PREFERRED EMBODIMENTS --.

Column 5,
Line 12, begin new paragraph with "Its".
Lines 60 and 61, after "plates." do not insert new paragraph.

Column 6,
Line 15, begin new paragraph with "This".
Line 64, begin new paragraph with "The".

Column 7,
Line 10, begin new paragraph with "Thereafter".

Signed and Sealed this

Twenty-third Day of September, 2003

JAMES E. ROGAN
*Director of the United States Patent and Trademark Office*